(12) United States Patent
Powell et al.

(10) Patent No.: US 8,168,137 B2
(45) Date of Patent: May 1, 2012

(54) NESTABLE, STACKABLE PIPETTE RACK FOR NESTABLE PIPETTE TIPS

(75) Inventors: William Ryan Powell, Loveland, CO (US); Ian Yates, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 425 days.

(21) Appl. No.: 12/131,304

(22) Filed: Jun. 2, 2008

(65) Prior Publication Data
US 2009/0293643 A1 Dec. 3, 2009

(51) Int. Cl.
*G01N 1/28* (2006.01)
(52) U.S. Cl. ...... 422/500; 422/68.1; 422/50; 73/863.01; 73/864.01; 206/505; 211/60.1
(58) Field of Classification Search .......... 422/68, 422/1, 99, 100, 63, 500; 211/60.1; 73/863.01, 73/864.01
See application file for complete search history.

(56) References Cited

U.S. PATENT DOCUMENTS

| | | | |
|---|---|---|---|
| 2,902,170 A * | 9/1959 | Miller | 211/72 |
| 4,349,109 A * | 9/1982 | Scordato et al. | 422/933 |
| 5,366,088 A | 11/1994 | Hill et al. | |
| 5,392,914 A | 2/1995 | Lemieux et al. | |
| 5,441,702 A | 8/1995 | Lemieux et al. | |
| 5,612,000 A | 3/1997 | Lemieux | |
| 5,779,984 A | 7/1998 | Kelly et al. | |
| 5,827,745 A * | 10/1998 | Astle | 422/100 |
| 6,007,779 A | 12/1999 | Lemieux et al. | |
| 6,063,579 A | 5/2000 | Bevirt et al. | |
| 6,325,114 B1 | 12/2001 | Bevirt et al. | |
| 6,534,015 B1 | 3/2003 | Viot et al. | |
| 6,666,644 B1 * | 12/2003 | Lind et al. | 414/798 |
| 2005/0150808 A1 * | 7/2005 | Sarna et al. | 206/562 |
| 2005/0255005 A1 | 11/2005 | Motadel | |
| 2007/0128084 A1 * | 6/2007 | Coassin et al. | 422/100 |

FOREIGN PATENT DOCUMENTS

| | | |
|---|---|---|
| EP | 0669856 | 4/1998 |
| JP | 8233829 | 9/1996 |
| WO | 03/64271 | 8/2003 |

* cited by examiner

*Primary Examiner* — In Suk Bullock
*Assistant Examiner* — Sharon Pregler

(57) ABSTRACT

The pipette rack comprises a plate, a peripheral base and a peripheral skirt. The plate has a first surface and defines an array of tip receptacles extending therethrough in a first direction orthogonal to the first surface. The tip receptacles are contoured to provide a clearance fit at locations axially offset from one another along a part of a pipette tip. The base extends in the first direction from the plate to a distal end surface. The skirt extends in the first direction from the base, and is outwardly offset therefrom to expose the distal end surface of the base so that the distal end surface contacts the plate of a similar pipette rack when the pipette racks are stacked.

21 Claims, 13 Drawing Sheets

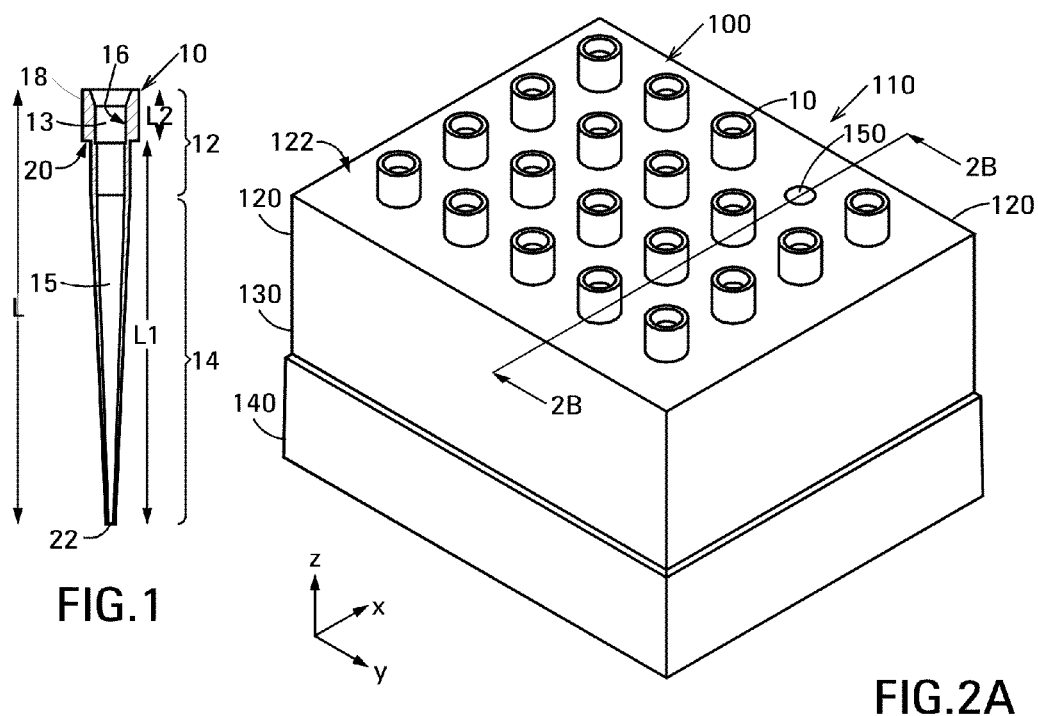
FIG.1
FIG.2A
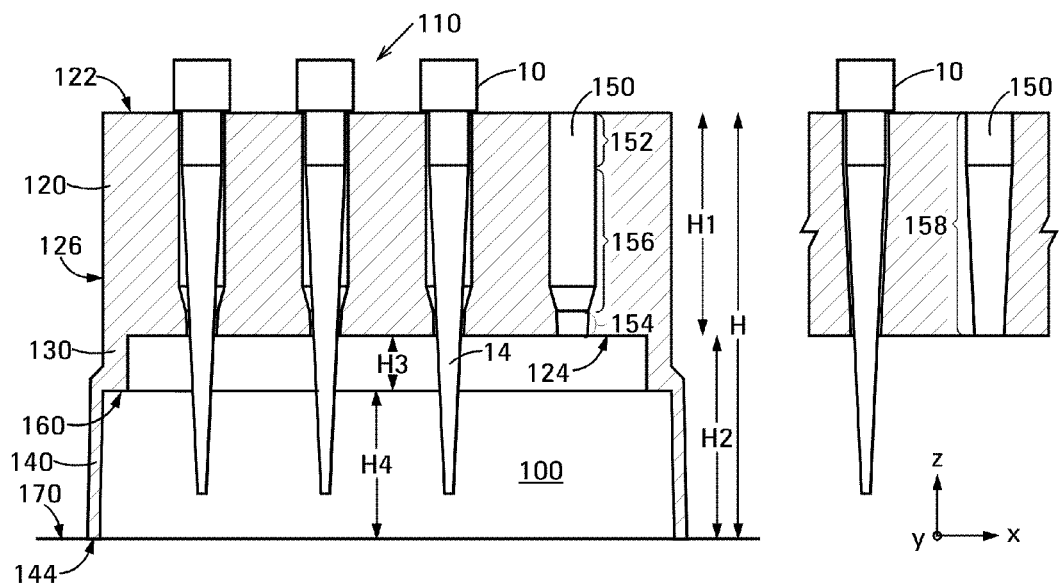
FIG.2B
FIG.2C

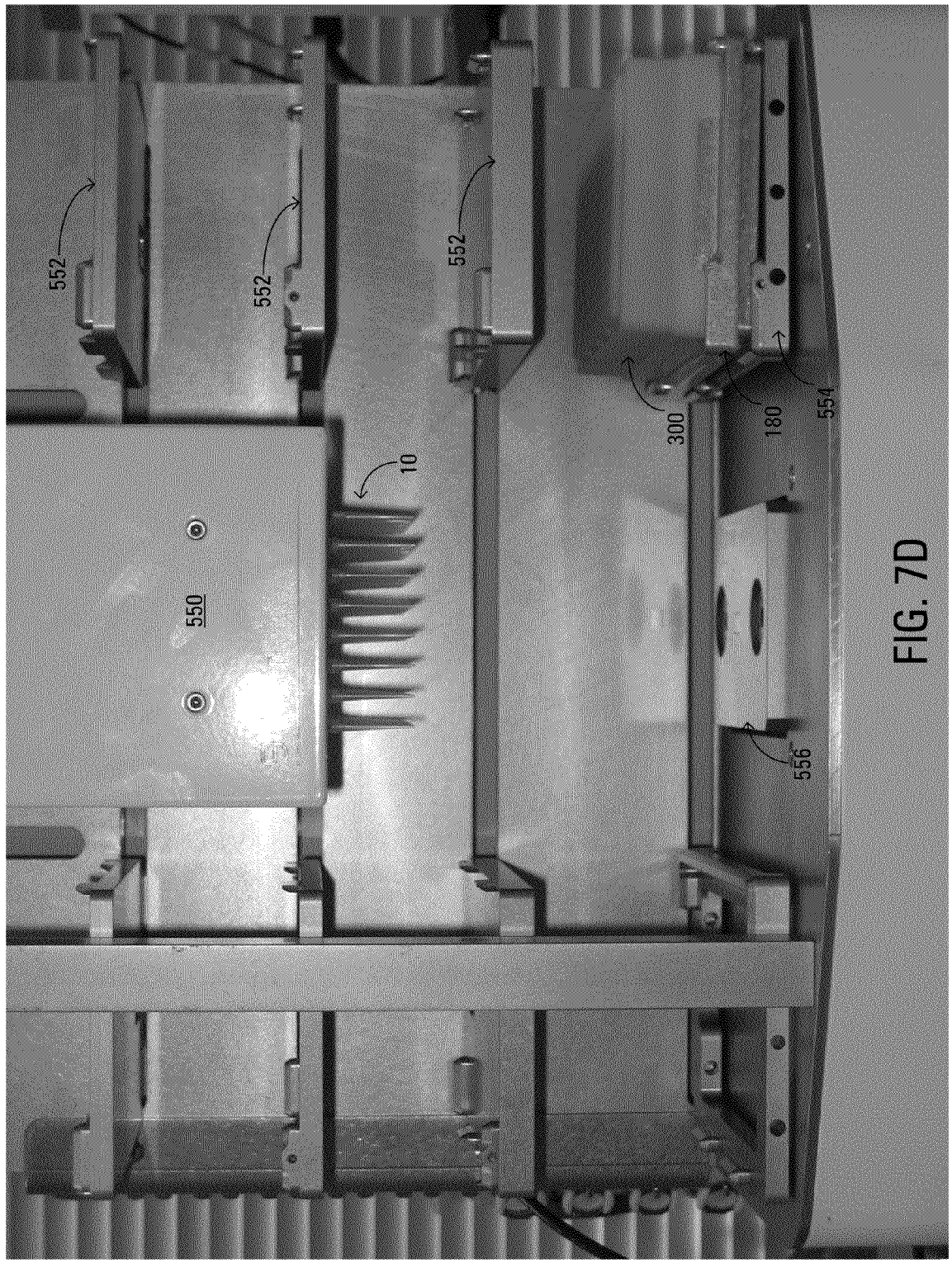

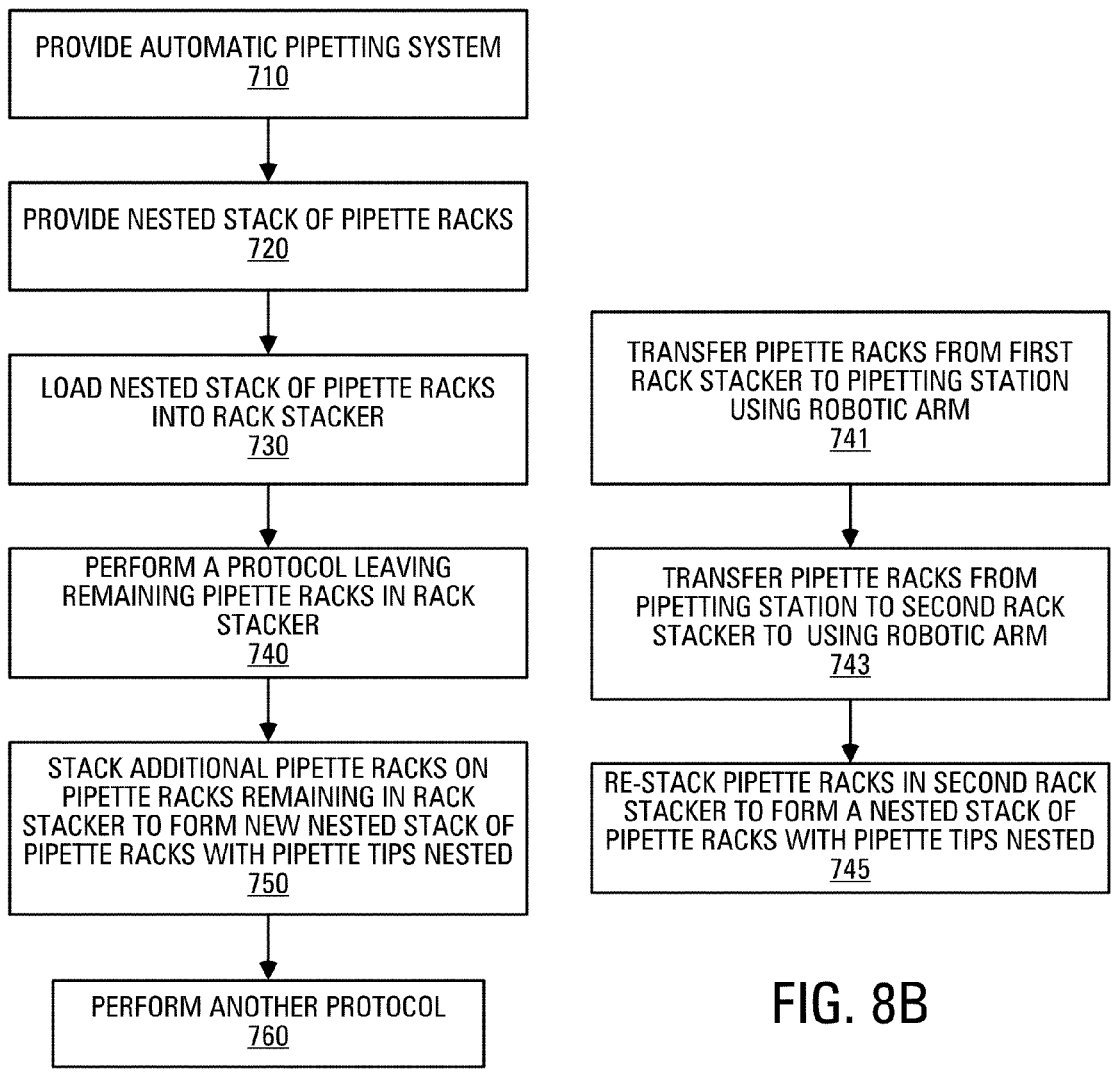

NESTABLE, STACKABLE PIPETTE RACK FOR NESTABLE PIPETTE TIPS

BACKGROUND

Automated pipetting stations are designed to transfer multiple measured aliquots of liquid from one multi-well plate to another multi-well plate. Such pipetting stations comprise a pipetting head capable of engaging with multiple disposable pipette tips. For convenience of handling, the pipette tips are supplied pre-loaded in a pipette rack.

FIG. 1 is a cross-sectional view showing an example of a typical pipette tip 10 suitable for use with an automated pipetting station. Pipette tip 10 has a neck portion 12 and a tapered portion 14. Neck portion 12 engages with a respective one of the barrels (not shown) of the pipetting head of the pipetting station. The pipetting head and its constituent barrels and the pipetting station are not shown in FIG. 1 but are described below with reference to FIG. 7A. Neck portion 12 is hollow and has an internal bore 13 whose diameter tapers from a maximum at the proximal end of pipette tip 10 and then remains substantially constant over the remaining length of the neck portion. The terms proximal and distal denote position relative to the pipetting head of the pipetting station. The constant-diameter portion of the bore 13 of neck portion 12 has a contoured inner surface 16 that provides positive engagement with the barrel of the pipetting head. The contouring is not shown to simplify the drawing. Tapered portion 14 extends axially from the neck portion 12. Tapered portion 14 is hollow and has a tapered bore 15. Tapered portion 14 and bore 15 have respective diameters that gradually reduce with increased distance from neck portion 12. At least part of neck portion 12 is surrounded by a collar 18. Collar 18 is larger in diameter than the neck portion 12 itself. Collar 18 has a distal surface 20 orthogonal to the longitudinal axis of pipette tip 10.

Pipette racks are supplied in pre-configured stacks of, for example, 20 pipette racks. Each pipette rack is pre-loaded with a defined number, e.g., 384, of pipette tips similar to pipette tip 10. To reduce the height of the stack of pipette racks, and, hence, the space needed to store the pipette tips, the pipette racks are configured to nest when they are stacked, and the pipette tips in each pipette rack nest in the pipette tips in the pipette rack below. The pipette racks nest in the sense that a lower part of an upper pipette rack accommodates an upper part of a lower pipette rack on which the upper pipette rack is stacked. The pipette tips nest in the sense that part of the tapered portion 14 of a pipette tip 10 in the upper pipette rack is located inside the neck portion 12 of a pipette tip 10 in the corresponding location in the lower pipette rack.

At the beginning of a protocol in which pipette tips are used, a stack of nested pipette racks is loaded into a rack stacker at the pipetting station. A robotic arm takes a pipette rack from the bottom of the stack and aligns the pipette rack with the pipetting head. The pipetting head moves downwards to engage with the pipette tips in the pipette rack, moves upwards to remove the pipette tips from the rack and then performs a liquid transfer process using the pipette tips. The pipetting head then moves downwards to return the used pipette tips to the rack. The robotic arm then discards the pipette rack holding the used pipette tips.

As noted above, it is advantageous to stack the pipette racks with the pipette racks and the pipette tips in a nesting arrangement to conserve packaging and storage space. However, when a conventional nestable, stackable pipette rack is stacked on another, similar pipette rack with the pipette tips in a nesting arrangement, the pipette tips tend to bind or cling to one another, resulting in one or more of the pipette tips being ejected from its rack. Ejected pipette tips are problematical because they can cause the equipment handling the pipette racks to jam.

When conventional nestable, stackable pipette racks are used, and there are not enough pipette racks remaining in the stack of pipette racks loaded in the rack stacker to perform the next protocol, the remainder of the stack of unused pipette racks is removed from the rack stacker and is discarded. A new stack of pipette racks is then loaded into the rack stacker and the next protocol is run. This wastage occurs because such conventional pipette racks are not configured to allow additional pipette racks to be added to a partial stack of pipette racks. Moreover, such conventional pipette racks cannot be re-stacked in another rack stacker after the pipette tips in them have been used. Consequently, such conventional pipette racks holding used pipette tips have to be discarded individually.

One solution to the problems of mechanical binding and electrostatic cling is to provide an intermediate tip support plate between the pipette racks to prevent the pipette tips from nesting too closely, if at all. The intermediate tip support plate increases the spacing between the pipette racks so that close nesting between the pipette tips does not occur. This allows the pipette racks to be stacked without mechanical binding or electrostatic attraction between the pipette tips that can lead to problems when such pipette racks are stacked. However, the intermediate tip support plate undesirably increases the stacking pitch, which decreases the number of pipette racks that can be stacked within a rack stacker of a given size and increases the storage space required to store a given number of pipette racks.

Accordingly, what is needed is a nestable, stackable pipette rack that allows maximum nesting of the pipette tips, that allows pipette racks to be added to a depleted stack of pipette racks prior to performing a protocol, and that allows pipette racks to be automatically re-stacked after the pipette tips in them have been used.

BRIEF DESCRIPTION OF THE DRAWINGS

FIG. 1 is a cross-sectional view of a pipette tip suitable for use in stackable pipette racks in which the pipette tips are nested.

FIGS. 2A and 2B are respectively an isometric view and a cross-sectional view showing a highly simplified example of a nestable, stackable pipette rack for nestable pipette tips in accordance with an embodiment of the invention.

FIG. 2C is a partial cross-sectional view showing an example of an alternative configuration of tip receptacle of the pipette rack shown in FIGS. 2A and 2B.

FIGS. 7A-7E are schematic drawings illustrating the operation of an automated pipetting system with nestable, stackable pipette racks in accordance with an embodiment of the invention.

FIGS. 8A and 8B are flow charts illustrating a method in accordance with an embodiment of the invention.

DETAILED DESCRIPTION

Figure 3A:
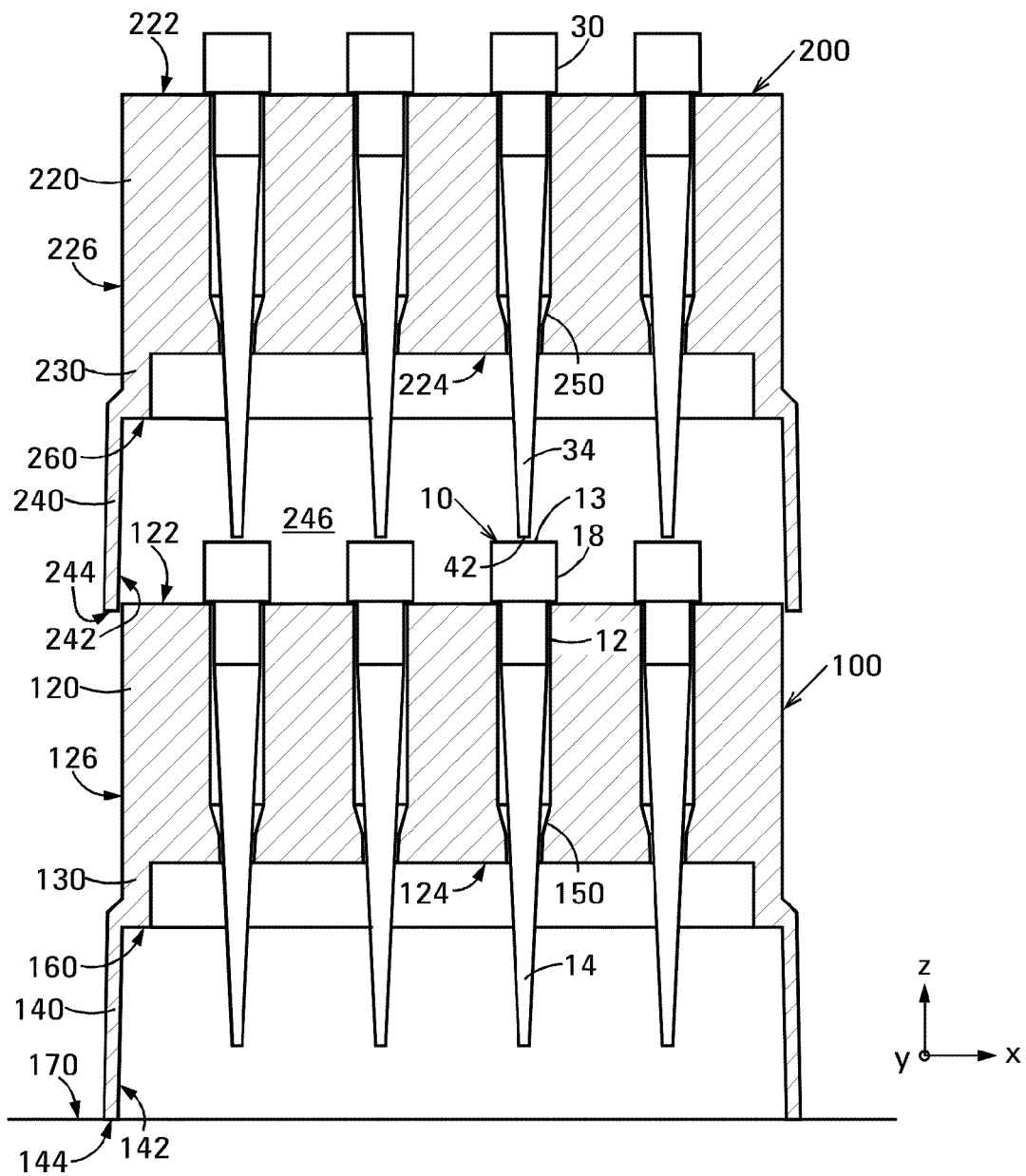
FIGS. 3A and 3B are cross-sectional views taken during the process of stacking another, similar pipette rack on the pipette rack shown in FIGS. 2A and 2B.

FIGS. 2A and 2B are respectively an isometric view and a cross-sectional view showing a highly simplified example of a nestable, stackable pipette rack 100 for nestable pipette tips in accordance with an embodiment of the invention. A typical example of pipette rack 100 accommodates 384 pipette tips in a 24×16 two-dimensional array. Pipette rack 100 is nestable in the sense that a stack of N pipette racks has a total height less than N times the height of an individual pipette rack. FIGS. 2A and 2B also show an example of a combination 110 in accordance with an embodiment of the invention. The combination is composed of nestable, stackable pipette rack 100 and a nestable pipette tip 10. Reference numeral 10 will also be used to refer to the pipette tips collectively.

Also shown in FIGS. 2A and 2B are three mutually-orthogonal directions, namely, an x-direction, a y-direction and a z-direction that will be used to describe pipette rack 100 and combination 10. FIG. 2B is enlarged relative to FIG. 2A to allow details to be clearly shown more clearly. Moreover, to simplify the drawing, the pipette tips are not shown in cross-section in FIG. 2B. Finally, FIGS. 2A and 2B show pipette rack 100 with no pipette tip in one of its tip receptacles to enable details of the unoccupied tip receptacle to be shown. Pipette rack 100 would normally have pipette tips in all of its tip receptacles.

The example of pipette rack 100 shown in FIGS. 2A and 2B is composed of a plate 120, a peripheral base 130 and a peripheral skirt 140. Plate 120 has a first surface 122 disposed parallel to the x-y plane, and a second surface 124 parallel to first surface 122. Plate 120 defines an array of tip receptacles that extend through the plate in the −z-direction, orthogonal to first surface 122. An exemplary tip receptacle is shown at 150. Reference numeral 150 will also be used to refer to the tip receptacles collectively. Tip receptacles 150 are configured to receive respective pipette tips 10, and each is contoured to provide a clearance fit at locations axially offset from one another along a part of a pipette tip located therein.

Base 130 extends in the −z-direction from plate 120 to a distal end surface 160, and skirt 140 also extends in the −z-direction from base 130 to a distal end surface 144. Skirt 140 is outwardly offset from base 120. The outward offset of skirt 140 exposes the distal end surface 160 of base 130, which allows distal end surface 160 to contact the plate of another, similar pipette rack when the pipette racks are stacked. Distal end surface 160 is disposed generally parallel to the x-y plane.

Pipette rack 100 will now be described in greater detail. As noted above, tip receptacle 150 defined in plate 120 is contoured to provide a clearance fit at locations axially offset from one another along the part of a pipette tip located in the tip receptacle. FIG. 2B shows the tapered portion 14 of pipette tip 10 located within tip receptacle 150, and tip receptacle 150 is contoured to provide a clearance fit in two regions 152, 154 axially offset from one another along the tapered portion 14 of pipette tip 10. Region 152 extends in the −z-direction into plate 120 from first surface 122. Region 154 extends in the +z-direction into plate 120 from second surface 124. Regions 152 and 154 are offset from one another in the z-direction, which corresponds to the axial direction of pipette tip 10 when the pipette tip is located in tip receptacle 150. In a region 156 between regions 152 and 154, the fit between tip receptacle 150 and pipette tip 10 is looser than the clearance fit within regions 152 and 154.

FIG. 2C is a partial cross-sectional view showing an example of an alternative configuration of tip receptacle 150. In this alternative configuration, tip receptacle 150 is contoured to provide a clearance fit in a single region 158 that extends along the entire length of the part of pipette tip 10 located within the tip receptacle. This alternative configuration of tip receptacle 150 is therefore contoured to provide a clearance fit at multiple locations axially offset from one another along the part of the pipette tip located within the tip receptacle.

The clearance fit provided by the contouring of tip receptacle 150 is designed such that, when pipette tip 10 is located in the tip receptacle, the clearance between the pipette tip and the tip receptacle is greater than zero for all combinations of the manufacturing tolerances of pipette tip 10 and tip receptacle 150. This allows the pipette tips to be inserted into and withdrawn from their respective tip receptacles in pipette rack 100 without mechanical binding between the pipette tips and their respective tip receptacles. The maximum size of the clearance fit depends on the nesting properties of pipette tip 10 and the stacking properties of pipette rack 100, as will be described below with reference to FIGS. 3A and 3B.

Adjacent the first surface 122 of plate 120, tip receptacle 150 has an inside diameter less than the outside diameter of the collar 18 of pipette tip 10 so that when pipette tip 10 is located in tip receptacle 150, the distal surface 20 of collar 18 rests on first surface 122. The remaining tip receptacles 150 are similarly dimensioned. Plate 120 has a height H1, i.e., dimension in the z-direction, less than the length L1 of pipette tip 10 from the distal surface 20 of collar 18 to the distal end 22 of pipette tip 10. Thus, a distal portion 22 of pipette tip 10 projects from the second surface 124 of plate 120 when pipette tip 10 is located in tip receptacle 150.

Base 130 and skirt 140 collectively extend from the second surface 124 of plate by a combined height H2 such that the overall height H (=H1+H2) of pipette rack 100 is greater than the overall length L of pipette tip 10, i.e., H>L. This relationship allows pipette rack 100 to stand on a plane surface 170 without the distal end 22 of pipette tip 10 contacting surface 170.

Pipette rack 100 is typically made by molding it from a suitable plastic, such as polypropylene. Plate 120, base 130 and skirt 140 are typically molded as a single unit, but can be molded as independent units. The independent units are then assembled by a technique such as snap fit, gluing or welding to form pipette rack 100. The process of molding plate 120 additionally defines tip receptacles 150 arrayed on arraying centers that match the arraying centers of the barrels constituting the pipetting head (not shown) with which pipette rack 100 is designed to inter-operate. In an embodiment, the process of molding plate 120 additionally defines blind recesses (not shown) extending into the plate from second surface 124. The blind recesses are centered between diagonally-adjacent ones of tip receptacles 150, and reduce the mass and improve the dimensional stability of plate 120.

Molding and, optionally, assembly techniques suitable for fabricating pipette rack 100 are known in the plastic fabrication art and will not be described here. Materials other than plastics may alternatively be used.

Figure 3B:
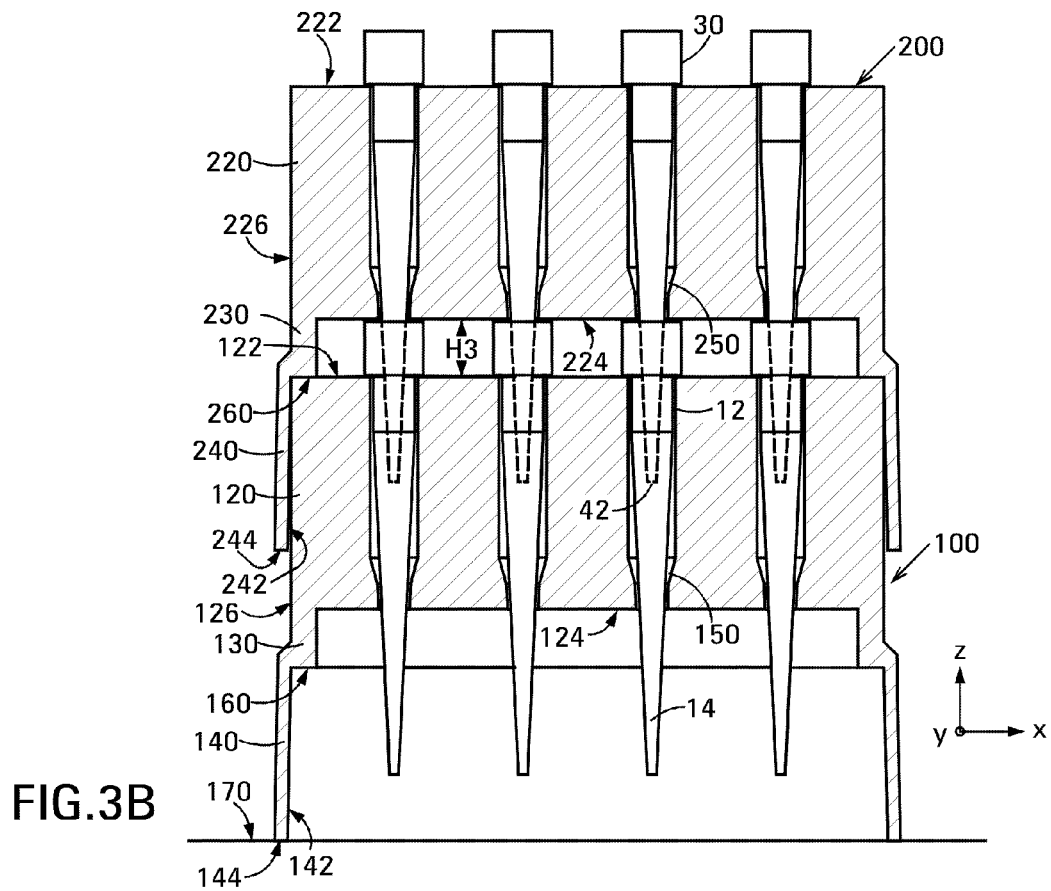

FIGS. 3A and 3B are cross-sectional views showing an example of another pipette rack 200 being stacked on top of pipette rack 100. Pipette rack 200 is identical to pipette rack 100 and is loaded with pipette tips an exemplary one of which is shown at 30. Reference numeral 30 will additionally be used to indicate the pipette tips in pipette rack 200 collectively. Each of the pipette tips 30 is nominally identical to pipette tip 10. Elements of pipette rack 200 corresponding to elements of pipette rack 100 are indicated using the same reference numerals with 100 added and will not be described in detail. Moreover, descriptions below of the features of pipette rack 200 also apply to the corresponding features of pipette rack 100.

The stacking process that is described next can be performed by hand or by a stacking mechanism such as that which constitutes part of a rack stacker. When the stacking operation is performed using a stacking mechanism, the stacking mechanism (not shown) is configured to keep the first surface 222 of pipette rack 200 oriented parallel to the x-y plane and to allow pipette rack 200 to move freely by small distances in the x- and y-directions. Regardless of what means is used to stack the pipette racks, one or more additional pipette racks (not shown) may already be stacked on top of pipette rack 200 when pipette rack 200 is stacked on pipette rack 100. Moreover, pipette rack 100 may be stacked on one or more other pipette racks when pipette rack 200 is stacked on top of it. Furthermore, instead of stacking pipette rack 200 on top of pipette rack 100, pipette rack 100 may be stacked under pipette rack 200. Finally, the nesting of the pipette tips in pipette rack 200 in the pipette tips in pipette tip 100 will be described with reference to the nesting of one exemplary pipette tip 30 in pipette rack 200 in one exemplary pipette tip 10 in pipette rack 100. The nesting of the remaining pipette tips in pipette rack 200 in respective ones of the remaining pipette tips in pipette rack 100 is similar and will therefore not be described.

FIG. 3A shows pipette racks 100 and 200 early in the stacking process. Pipette rack 200 has been aligned relative to pipette rack 100 in the x-y plane such that the opening 246 bounded by the skirt 240 of pipette rack 200 is aligned with the plate 120 of pipette rack 100. Additionally, pipette rack 200 has been lowered slightly in the −z-direction so part of plate 120 has entered opening 246. Since the overall height of pipette rack 200 is greater than the overall length of pipette tips 30, plate 120 must enter opening 246 before the distal end 42 of pipette tip 30 in pipette rack 200 can enter the bore 13 of the neck portion 12 of the respective pipette tip 10 in pipette rack 100. Plate 120 cannot enter opening 246 unless pipette rack 200 is positioned in the x-y plane and in rotation such that skirt 240 is aligned with the plate. Aligning pipette rack 200 in the x-y plane such that plate 120 can enter opening 246 automatically aligns the distal end 42 of pipette tip 30 in pipette rack 200 with the bore 13 of the corresponding pipette tip 10 in pipette rack 100 such that pipette tip 30 is nominally aligned coaxially with pipette tip 10. This alignment prevents contact between the distal end 42 of pipette tip 30 and the proximal end of the collar 18 of pipette tip 10. As a result, when pipette rack 200 is further lowered in the −z-direction, pipette tip 30 nests in pipette tip 10 with no significant physical contact between pipette tip 30 and pipette tip 10. Preventing such physical contact prevents pipette tip 30 from moving in the z-direction relative to pipette rack 200. Such movement of pipette tip 30 could eject pipette tip 30 from pipette rack 200 or could mis-align pipette tip 30 in pipette rack 200, either of which could cause jamming when an additional pipette rack is stacked on pipette rack 200.

Skirt 240 has a inside surface 242 that, at the proximal end of skirt 240 adjacent base 230, provides a clearance fit with the external surface 126 of the plate 120 of pipette rack 100. This clearance fit accurately defines the location of pipette rack 200 relative to pipette rack 100 in the x-y plane and in rotation when pipette rack 200 is stacked on pipette rack 100, as will be described below with reference to FIG. 3B. To make easier to achieve the initial alignment of the skirt 240 of pipette rack 200 with the plate 120 of pipette rack 100, the inside surface 242 of skirt 240 flares outward slightly with increasing distance from base 230. In the example shown in FIGS. 3A and 3B, skirt 240 has a non-tapered cross-sectional shape and skirt 240 flares outwards as a whole. Alternatively, in a manner similar to that described below with reference to FIG. 5B, skirt 240 has a cross-sectional shape that tapers towards the distal end 244 of skirt 240 such that inside surface 242 flares outwards. The above description of the inside surface 242 of skirt 240 additionally applies to the inside surface 142 of skirt 140.

As noted above, the tip receptacles 150 in pipette rack 100 and the tip receptacles 250 in pipette rack 200 are contoured to provide a clearance fit at locations axially offset from one another along the parts of pipette tips 10 or pipette tips 30, respectively, located therein. The closeness of the clearance fit depends on a number of factors. When the pipetting head engages with the pipette tips, the barrels of the pipetting head impose a displacement in the x-y plane on the respective pipette tips with which they engage. This is due to tolerances in the locations in the x-y plane of the individual barrels. The clearance fit cannot be so close that the displacement of the pipette tips causes one or more of the pipette tips to bind with its respective tip receptacle. On the other hand, too loose a clearance fit allows the pipette tips to deviate from their nominal positions in the x-y plane, which would increase the risk of significant physical contact between pipette tips when the pipette racks are stacked. Moreover, the flaring of the inside surface 242 of skirt 240 allows pipette rack 200 to deviate from its nominal alignment in the x-y plane relative to pipette rack 100, especially at the beginning of the stacking process shown in FIG. 3A due to the outward flare of inside surface 242. Taking into account the outward flare of inside surface 242, the clearance fit should not be so loose as to allow significant physical contact between pipette tips 30 in pipette rack 200 and pipette tips 10 in pipette rack 100 during relative motion in the z-direction between pipette rack 200 and pipette rack 100.

FIG. 3B shows pipette rack 100 and pipette rack 200 at the end of the stacking process. The distal end surface 260 of the base 230 of pipette rack 200 rests on the first surface 122 of the plate 120 of pipette rack 100. Contact between end surface 260 and first surface 122 defines the location of pipette rack 200 relative to pipette rack 100 in the z-direction. Although the inside surface 242 of the skirt 240 of pipette rack 200 has a clearance fit with the outside surface 126 of the plate 120 of pipette rack 100, inside surface 242 typically makes contact with outside surface 126 at about four spatially-separated locations. Contact between the inside surface 242 of skirt 240 and the outside surface 126 of plate 120 defines the location of pipette rack 200 relative to pipette rack 100 in the x-y plane and in rotation. Pipette tip 30 in pipette rack 200 is nested within corresponding pipette tip 10 in pipette rack 100 without physical contact between them. Moreover, since there was no contact between the pipette tips during the stacking process, the stacking process has not dislodged pipette tip 30 from its tip receptacle 250 in pipette rack 200. Nesting part of pipette rack 100 in part of pipette rack 200 and nesting part of pipette tip 30 in part of pipette tip 10 allows pipette racks 100 and 200 to be stacked with a stacking pitch that is less than the overall length of the pipette tips. In an example, pipette racks of pipette tips having an overall length L (FIG. 1) of 26 mm were stacked with a stacking pitch of about 17 mm, i.e., the distance between first surface 122 and first surface 222 when pipette rack 200 was stacked on pipette rack 100 was about 17 mm.

Base 230 extends from the second surface 224 of plate 220 such its height H3 (z-direction dimension) between second surface 224 and distal end surface 260 is greater than the maximum length L2 (axial dimension, shown in FIG. 1) of the collar 18 of pipette tip 10. This prevents contact between second surface 224 and the proximal end of pipette tip 10 in pipette rack 100. Such contact is undesirable because it could cause pipette tip 10 to deviate from its nominal alignment in tip receptacle 150. In the example shown in FIG. 3B, the clearance between the proximal end of pipette tip 10 and second surface 224 is no more than that which accommodates the maximum length of collar 18. In examples in which the pipette tips cannot be nested as closely as those exemplified in FIG. 3B, base 230 is configured such that its height H3 between second surface 224 and distal end surface 260 is greater than that shown, and the height H4 (z-direction dimension) of skirt 240 from the distal end surface 260 of base 230 to the distal end surface 244 of the skirt 240 is correspondingly less than that shown so that the relationship between the overall height H of pipette rack 200 and the length L of pipette tip 30 remains unchanged.

The configuration of pipette rack 100 and pipette rack 200 enables the pipette racks to be easily stacked and re-stacked. This allows pipette racks to be added to a partially-depleted stack of pipette racks as needed. The ability to add pipette racks to an existing stack of pipette racks, either manually or mechanically with a robotic arm, reduces the wastage of perfectly usable new pipette racks by upwards of 30%. The configuration of pipette rack 100 and pipette rack 200 also allows the pipette racks to be manually or automatically re-stacked after the pipette tips in them have been used.

Engaging the pipetting head (not shown) of the pipetting station with the pipette tips 10 in a typical embodiment of pipette rack 100 capable of holding 384 pipette tips subjects the pipette tips and, hence, plate 120 to an engagement force in the z-direction. In a typical example, the maximum engagement force is about 275 kg. Applying the engagement force to plate 120 with the distal end surface 144 of skirt 140 in contact with plane surface 170 incurs a significant risk of breaking either or both of skirt 140 and the offset junction between base 130 and skirt 140. This is because skirt 140 is outwardly flared, has relatively thin wall and is outwardly offset from base 130 at a relatively abrupt junction.

Figure 4:
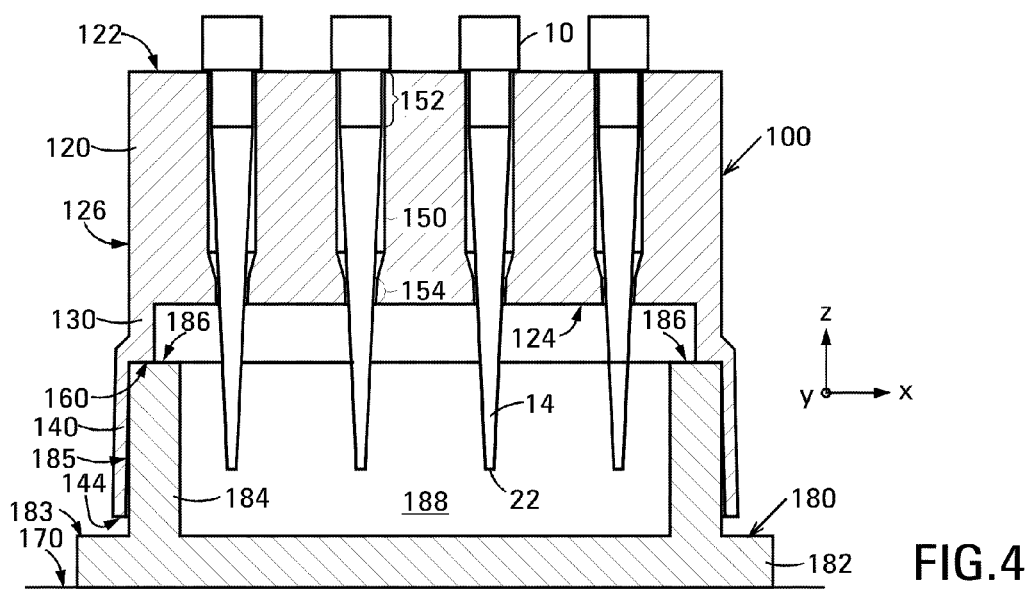
FIG. 4 is a cross-sectional view showing the pipette rack shown in FIGS. 2A and 2B stacked on an example of a station base.

FIG. 4 is a cross-sectional view of pipette rack 100 mounted on a station adapter 180 that constitutes part of the pipetting station and allows the pipetting head to engage with the pipette tips in pipette rack 100 with a minimal risk of damage to the pipette rack. Station adapter 180 is composed of a base plate 182 and an engaging portion 184.

Base plate 182 has opposed plane surfaces parallel to the x-y plane. Base plate 182 is shaped and dimensioned to mount on the press shelf of the pipetting station, described below with reference to FIGS. 7A-7E, at a position accurately defined at least in the x-y plane.

Engaging portion 184 extends in the z-direction from the upper surface 183 of base plate 182 and terminates in a plane end surface 186 parallel to the x-y plane. Engaging portion 184 has a hollow interior 188 in which the distal ends 22 of the pipette tips 10 mounted in pipette rack 100 are located when pipette rack 100 is mounted on station adapter 180. Engaging portion 184 is dimensioned such that the height (z-direction dimension) of the end surface 186 of engaging portion 184 above the upper surface 183 of base plate 182 is greater than the height of the distal end surface 160 of base 130 above the distal end surface 144 of skirt 140. This dimensional relationship ensures that, when pipette rack 100 is mounted on station adapter 180, the end surface 186 of engaging portion 184 will contact distal end surface 160 of base 130, and that the distal end surface 144 of skirt 140 will not contact the upper surface 183 of base plate 182. Engaging portion 184 has an outside surface 185 shaped and dimensioned to provide a clearance fit with the skirt 140 of pipette rack 100 when pipette rack 100 is mounted on station adapter 180 with the end surface 160 of the base 130 of the pipette rack in contact with the end surface 186 of engaging portion 184.

Pipette rack 100 is mounted on station base 180 in the pipetting station before the pipetting head of the pipetting station engages with the pipette tips 10 in pipette rack 100. Mounting pipette rack 100 on station base 180 brings the end surface 160 of base 130 into contact with the end surface 186 of the engaging portion 182 of station adapter 180, which accurately defines the location of pipette rack 100 in the z-direction. The clearance fit between the outside surface 185 of engaging portion 184 and the inside surface 142 of skirt 140 accurately defines the location of pipette rack 100 relative to the pipetting head in the x-y plane and in rotation. Additionally, contact between the distal end surface 160 of base 130 and the end surface 186 of the engaging portion 184 of station base 180 transfers the force applied to plate 120 by engaging the pipetting head with pipette tips 10 to station adapter 180 via base 130. Unlike skirt 140, base 130 is sufficiently sturdy and is structurally connected to plate 120 in a manner that allows base 130 to transfer the engagement force of several hundred kilograms to its distal end surface 160 with a minimum risk of damage.

Figure 5A:
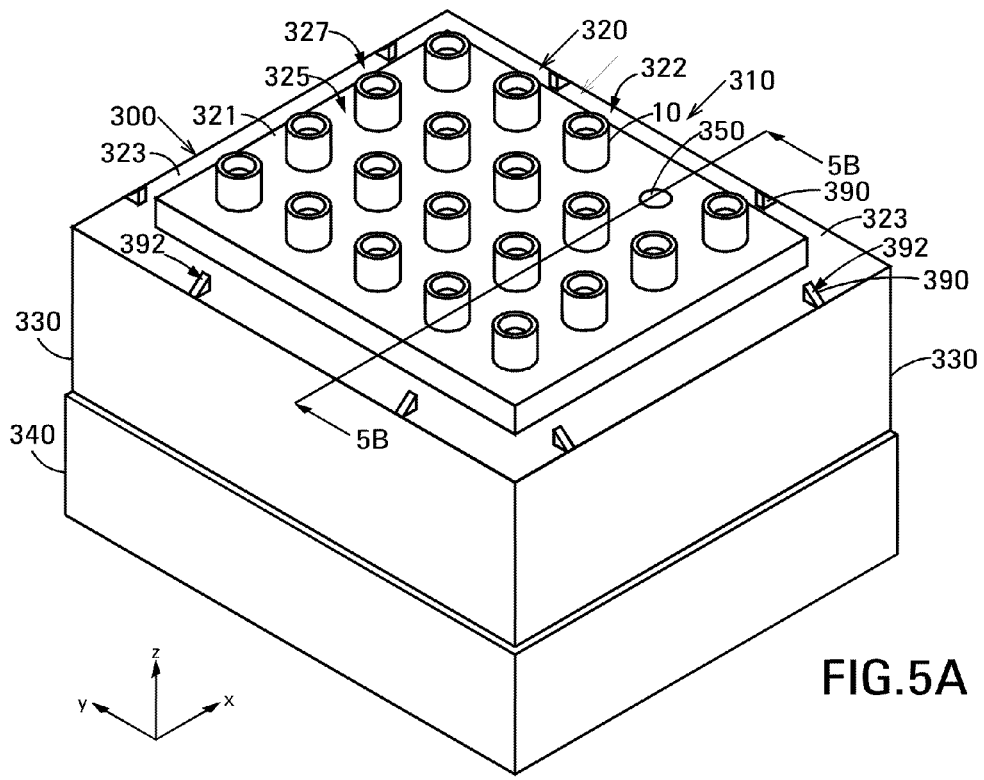
FIGS. 5A and 5B are respectively an isometric view and a cross-sectional view showing another highly simplified example of a nestable, stackable pipette rack for nestable pipette tips in accordance with an embodiment of the invention.
Figure 5B:
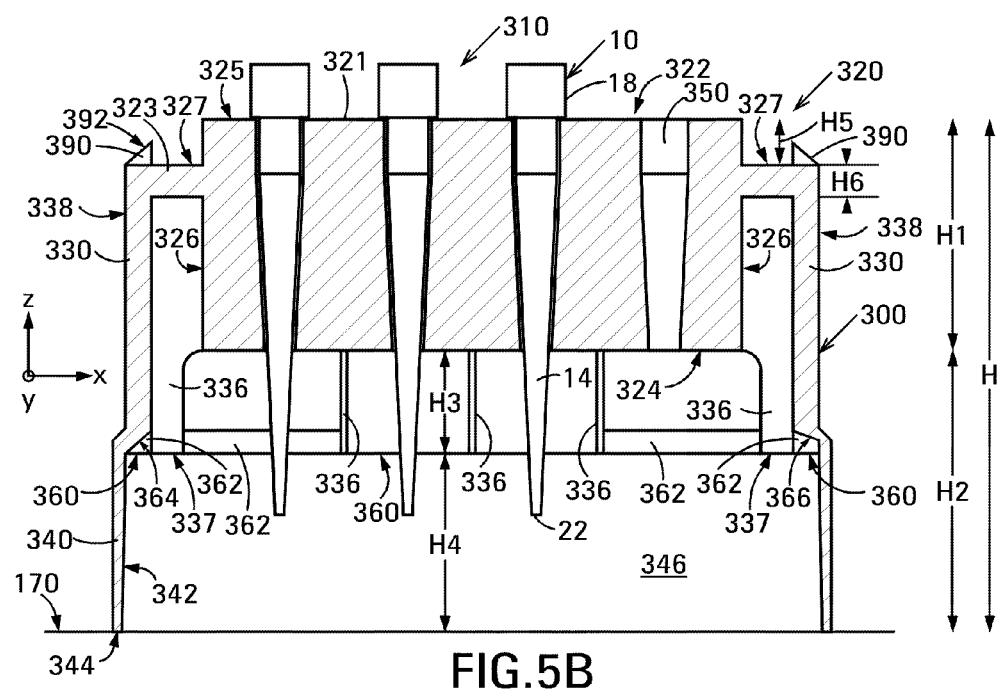

FIGS. 5A and 5B are respectively an isometric view and a cross-sectional view showing another highly simplified example of a nestable, stackable pipette rack 300 for nestable pipette tips in accordance with an embodiment of the invention. A typical example of pipette rack 300 accommodates 384 pipette tips in a 24×16 two-dimensional array. FIGS. 5A and 5B also show an example of a combination 310 in accordance with an embodiment of the invention. The combination is composed of nestable, stackable pipette rack 300 and a nestable pipette tip 10. Pipette rack 300 differs from pipette rack 100 in that it is configured to conform with industry standard dimensions for microtitre plates, and to permit its use in a process known as serial dilution. Pipette rack 300 additionally has stacking guides that further facilitate nested stacking.

FIG. 5B is enlarged relative to FIG. 5A to allow some details to be clearly shown more clearly. Moreover, to simplify the drawing, the pipette tips are not shown in cross-section in FIG. 5B. Finally, FIGS. 5A and 5B show pipette rack 300 with no pipette tip in one of its tip receptacles to enable details of the unoccupied tip receptacle to be shown. Pipette rack 300 would normally have pipette tips in all of its tip receptacles.

The example of pipette rack 300 shown in FIGS. 5A and 5B is composed of a plate 320, a peripheral base 330 and a peripheral skirt 340. Plate 320 has a first surface 322 disposed parallel to the x-y plane, and a second surface 324 parallel to first surface 322. Plate 320 defines an array of tip receptacles that extend through the plate in the −z-direction, orthogonal to first surface 322. An exemplary tip receptacle is shown at 350. Reference numeral 350 will also be used to refer to the tip receptacles collectively. Tip receptacles 350 are configured to receive respective pipette tips 10, and are each contoured to provide a clearance fit at locations axially offset from one another along a part of a pipette tip located therein.

In pipette rack 300, plate 320 is composed of an inner plate 321 and an outer plate 323. Outer plate 323 is disposed around inner plate 321. In the example shown, outer plate 323 is disposed around inner plate 321 on all four sides. In other examples, outer plate 323 is disposed around inner plate 321 on fewer than four sides, or is even located on only one side of inner plate 321. Tip receptacles 350 are defined only in inner plate 321. Outer plate 323 laterally extends the dimensions of plate 320 beyond those of inner plate 321 in which the tip receptacles are located such that the external dimensions of pipette rack 300 conform with the above-mentioned industry standard dimensions.

In pipette rack 300, the first surface 322 of plate 320 is composed of an inner first surface 325 and an outer first surface 327. Inner first surface 325 is the first surface of inner plate 321. Outer first surface 327 is the first surface of outer plate 323. Outer first surface 327 is offset in the −z-direction relative to inner first surface 325.

Stacking guides 390 are located at the perimeter of outer plate 323, specifically on outer first surface 327, and extend inwards towards inner plate 321. Each stacking guide has a guide surface 392 that slopes upwards from outer first surface 327 and inwards towards inner plate 321. In the example shown, the slope of guide surface 392 is linear. Other slope characteristics are possible. Stacking guides similar to stacking guides 390 may also be located around the perimeter of the first surface 122 of the plate of the example of pipette rack 100 described above with reference to FIGS. 2A and 2B.

Base 330 extends in the −z-direction from the perimeter of outer plate 321 to a distal end surface 360.

In the example shown in FIGS. 5A and 5B, the height (z-direction dimension) H6 of outer plate 323 is significantly less than the height H1 of inner plate 321. To transfer part of the above-described pipette tip engagement force of several hundred kilograms from inner plate 321, where the pipette tips are located, to a station base on which pipette rack 300 is mounted when subject to the engagement force, buttresses 336 located at intervals around the exterior of inner plate 321 extend orthogonally from the side surface 326 of inner plate 321 to outer plate 323 and base 330. Buttresses 336 each extend in the −z-direction to a respective end surface 337 flush with the distal end surface 360 of base 330.

In the pipetting station (not shown), pipette rack 300 is stacked on an embodiment of station adapter 180 described above with reference to FIG. 4 before the pipetting head (not shown) engages with pipette tips 10. Referring additionally to FIG. 4, in an embodiment of station adapter 180 suitable for use with pipette rack 300, the end surface 186 of engaging portion 184 is sufficiently wide that both the distal end surface 360 of base 330 and the end surfaces 337 of buttresses 336 contact end surface 186. Buttresses 336 directly transfer part of the engagement force applied in the −z-direction to inner plate 321 to station adapter 180 when the pipetting head engages with the pipette tips 10 in pipette rack 300. The remainder of the engagement force is transferred from inner plate 323 to station adapter 180 by outer plate 323 and base 330, and buttresses 336 additionally resist the torque applied to base 330 as a result of the lateral offset of base 330 from inner plate 321.

Skirt 340 extends in the −z-direction from the distal end of base 330 to a distal end surface 344. Skirt 340 is outwardly offset from base 330. The outward offset of skirt 340 from base 330 exposes the distal end surface 360 of base 330, which allows distal end surface 360 to contact the outer plate of another, similar pipette rack when the pipette racks are stacked. The distal end surface 360 of base 330 is a surface located at the distal end of base 330 remote from outer plate 323. Distal end surface 360 is disposed parallel to the x-y plane but is interrupted at several locations along its length by recessed regions 362. The plane in which the cross-section shown in FIG. 5B is taken intersects pipette rack 300 in two of the recessed regions 362. One example of recessed region 362 is shown at 364, where recessed region 362 is defined by chamfering base 330 to define a surface disposed at an acute angle to the x-y plane. Another example of recessed region 362 is shown at 366, where recessed region 332 is defined by rebating base 330 to define a surface offset from distal end surface 360 in the z-direction. The cross-sectional view shown in FIG. 5B also shows portions of end surface 360 offset in the y-direction from recessed regions 364 and 366. FIG. 5B shows the two instances of recessed region 362 as having different configurations 364, 366 merely for the sake of illustration. Typically, all instances of recessed region 362 are configured alike.

When another, similar pipette rack is stacked on pipette rack 300, as will be described below with reference to FIGS. 6A-6C, the distal end surface of the base of the other pipette rack and the distal ends of the buttresses of the other pipette rack rest on the outer first surface 327 of pipette rack 300 to define the spatial relationship between the pipette racks in the z-direction. The recessed regions of the base of the other pipette rack accommodate the stacking guides 390 of pipette rack 300, as will be described in more detail below with reference to FIG. 6C.

Alternatively, the height (z-direction dimension) H6 of outer plate 323 is less than the height H1 of inner plate 321 by difference equal to the z-direction offset H5 between inner first surface 325 and outer first surface 327. In this case, the height of base 330 is substantially less than that in the example shown in FIG. 5B, and the engagement force does not subject base 330 to a torque. These factors make buttresses 336 unnecessary, but the mass of such an embodiment of pipette rack 330 would be greater than that of the example shown.

Pipette rack 300 will now be described in greater detail. As noted above, tip receptacle 350 defined in inner plate 321 is contoured to provide a clearance fit at locations axially offset from one another along the part of pipette tip 10 located therein. In the example shown in FIG. 5B, tip receptacle 350 is contoured to provide a clearance fit in a single region that extends along the entire part of pipette tip 10 located within the tip receptacle, in a manner similar to that described above with reference to FIG. 2C. Tip receptacle 350 is therefore contoured to provide a clearance fit at locations axially offset from one another along the part of the pipette tip located therein. Tip receptacle 350 may alternatively be contoured to provide a clearance fit with pipette tip 10 in two axially-offset regions in a manner similar to that described above with reference to FIG. 2B.

Adjacent the first surface 322 of plate 320, tip receptacle 350 has an inside diameter less than the outside diameter of the collar 18 of pipette tip 10 so that when pipette tip 10 is located in tip receptacle 350, the distal surface 20 (FIG. 1) of collar 18 rests on inner first surface 325. The remaining tip receptacles 350 are similarly dimensioned. The height H1 of inner plate 321 is less than the length L1 of pipette tip 10 (FIG. 1) from the distal surface 20 of collar 18 to the distal end 22 of pipette tip 10. Thus, a distal portion of pipette tip 10 projects from the second surface 324 of inner plate 321 when pipette tip 10 is located in tip receptacle 350.

The distal end surface 344 of skirt 340 is offset in the −z-direction relative to the second surface 324 of inner plate 321 by a height H2 such that the overall height H (=H1+H2) of pipette rack 300 is greater than the overall length L of pipette tip 10, i.e., H>L. This relationship allows pipette rack 300 to stand on plane surface 170 without the distal end 22 of pipette tip 10 contacting surface 170.

As noted above, the plate 320 of pipette rack 300 is configured such that outer first surface 327 is offset in the −z-direction relative to inner first surface 325 to enable pipette rack 300 to be used in an operation known as serial dilution. In a serial dilution operation, the pipette rack is positioned relative to the pipetting head of the pipetting station such that only a single edge row or a single edge column of the barrels of the pipetting head engages with a corresponding single edge row or single edge column of the pipette tips in the pipette rack. In an example, the single row of barrels at the left-hand side of the pipetting head engages with the single row of pipette tips at the right-hand side of pipette rack 300. At least one row of unengaged barrels overlaps part of the pipette rack. When the barrels of the pipetting head engage with the pipette tips in the pipette rack, the distal ends of the barrels penetrate into the pipette tips to a level below that of inner first surface 325 of the pipette rack. During use of the pipette rack in operations other than serial dilution, every barrel of the pipetting head engages with a respective pipette tip in the pipette rack, and the barrels can penetrate to a level below that of inner first surface 325 unimpeded. However, in serial dilution in which some of the barrels of the pipetting head do not engage with respective pipette tips but nevertheless overlap outer first surface 327, if outer first surface 327 were flush with inner first surface 325, contact between the distal ends of the unengaged barrels and outer first surface 327 would prevent the barrels that engage with respective pipette tips from penetrating the pipette tips to the required depth. The offset in the −z-direction of outer first surface 327 relative to inner first surface 325 allows the single row or column of barrels of the pipetting head to penetrate the single row or column of pipette tips to the required depth without the distal ends of the unengaged barrels coming into contact with outer first surface 327. Outer first surface 327 is offset in the −z-direction below inner first surface 325 by a height H5 greater than the maximum depth of penetration of the distal ends of the barrels of the pipetting head below inner first surface 325.

Pipette rack 300 is typically made by molding it from a suitable plastic, such as polypropylene. Plate 320, including inner plate 321 and outer plate 323, base 330, buttresses 336, when present, skirt 340 and stacking guides 390 are typically molded as a single unit, but can be molded as independent units and assembled by a technique such as snap fit, fastening, gluing or welding. The process of molding inner plate 321 additionally defines tip receptacles 350 arrayed on arraying centers that match the arraying centers of the barrels of the pipetting head (not shown) with which pipette rack 300 is designed to inter-operate. In an embodiment, the process of molding inner plate 321 additionally defines blind recesses (not shown) extending into the inner plate from second surface 324. The blind recesses are centered between diagonally-adjacent ones of tip receptacles 350, and reduce the mass and improve the dimensional stability of plate 320.

Molding and, optionally, assembly techniques suitable for fabricating pipette rack 300 are known in the plastic fabrication art and will not be described here. Materials other than plastics may alternatively be used.

Figure 6A:
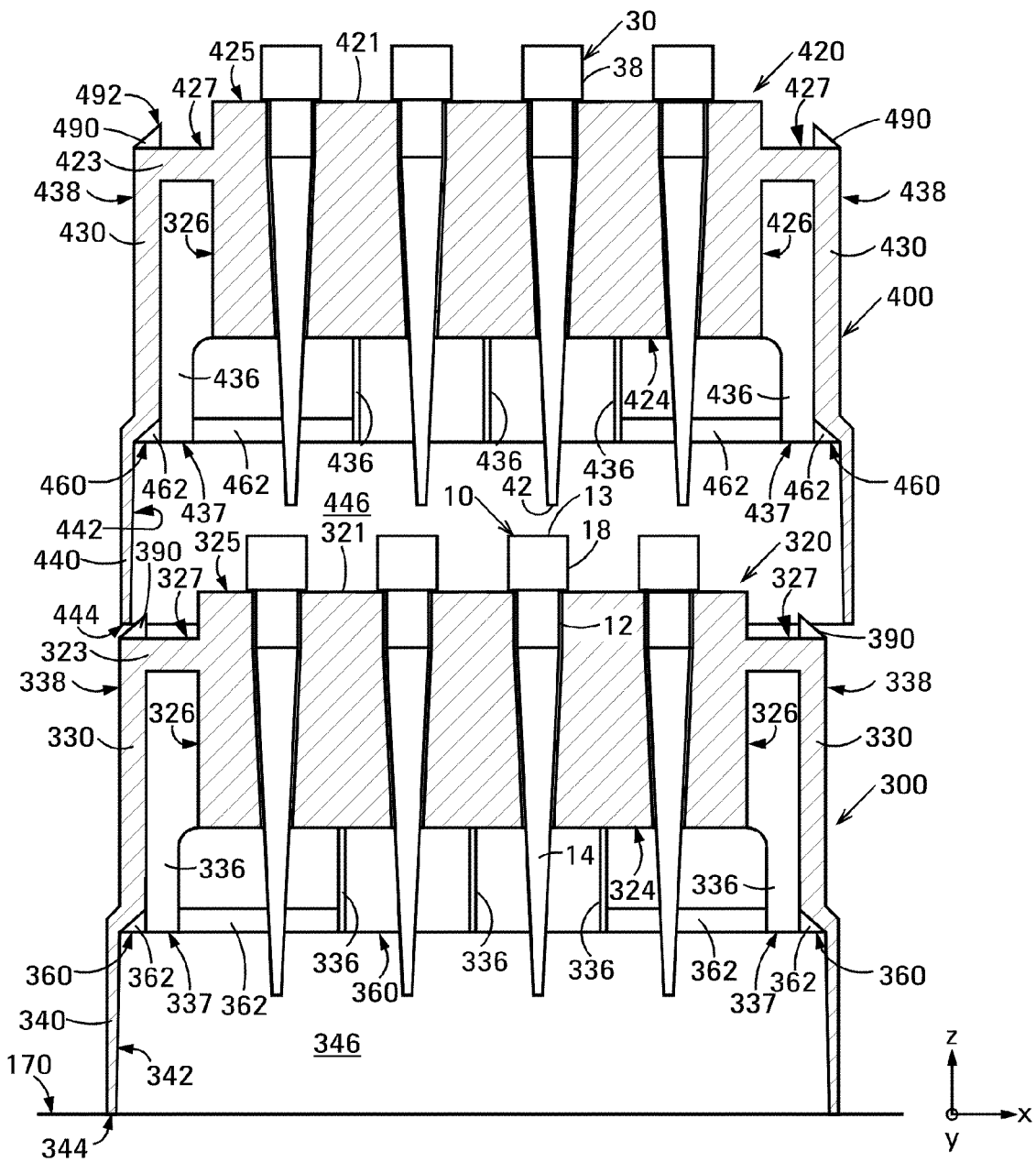
FIGS. 6A, 6B and 6C are cross-sectional views taken during the process of stacking another, similar pipette rack on the pipette rack shown in FIGS. 5A and 5B.
Figure 6B:
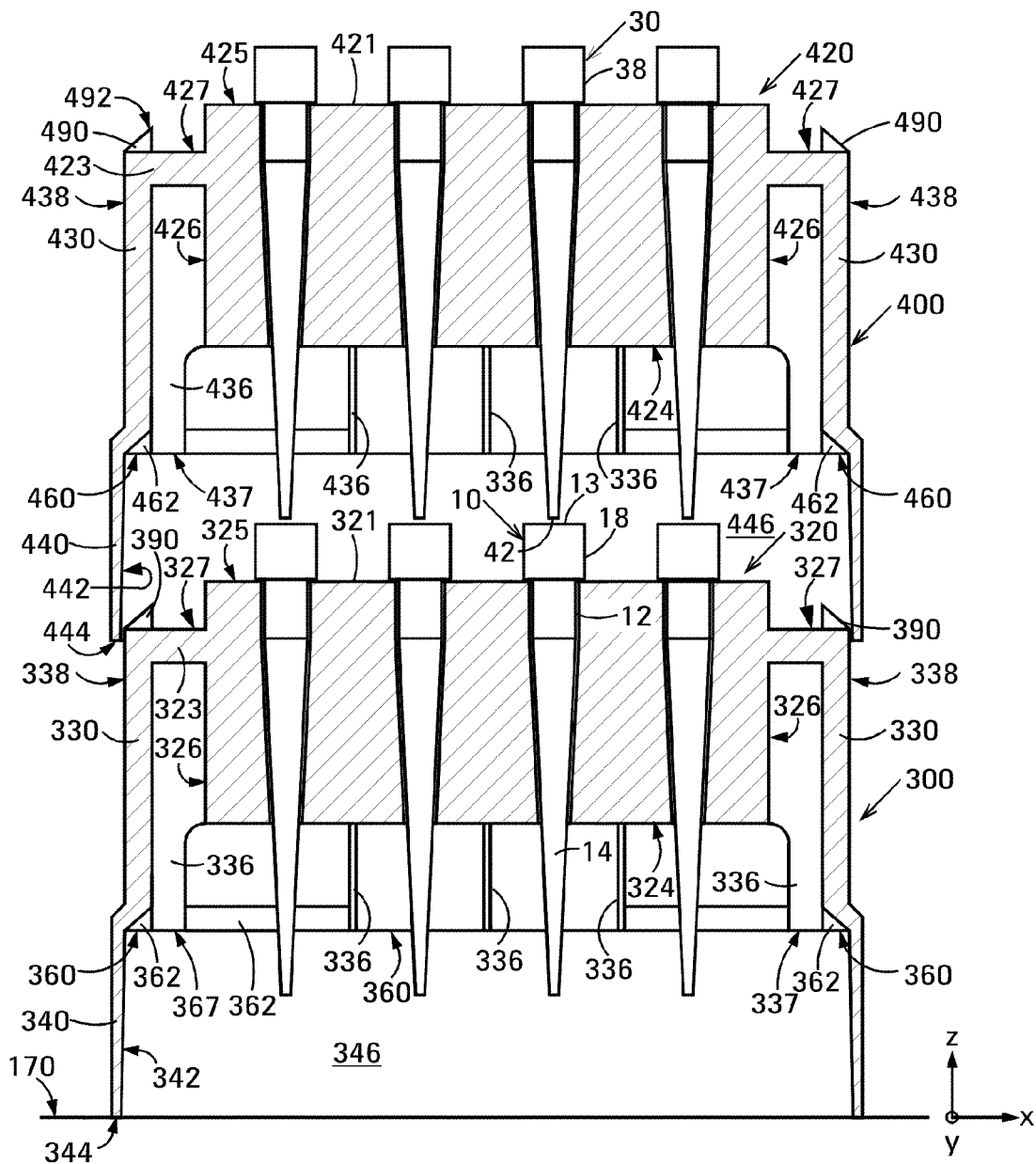
Figure 6C:
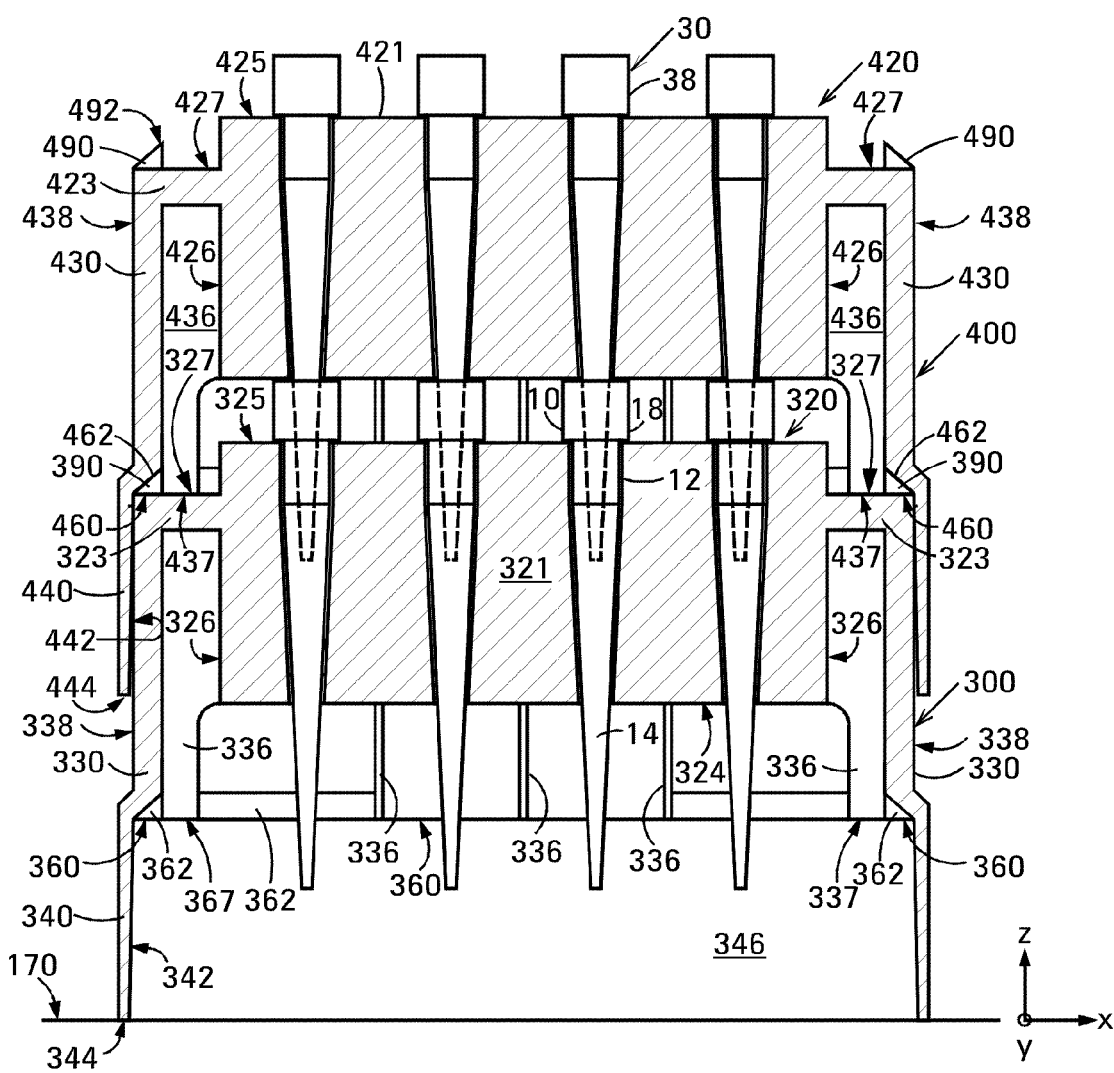

FIGS. 6A, 6B and 6C are cross-sectional views showing an example of another pipette rack 400 being stacked on top of pipette rack 300. Pipette rack 400 is identical to pipette rack 300 and is loaded with pipette tips 30, each of which is identical to pipette tip 10. Elements of pipette rack 400 corresponding to elements of pipette rack 300 are indicated using the same reference numerals with 100 added and will not be described in detail. Moreover, descriptions below of the features of pipette rack 400 also apply to the corresponding features of pipette rack 300.

The stacking process that is described next can be performed by hand or by a stacking mechanism such as that which constitutes part of a rack stacker. When the stacking operation is performed using a stacking mechanism, the stacking mechanism (not shown) is configured to keep the first surface 422 of pipette rack 400 oriented parallel to the x-y plane and to allow pipette rack 400 to move freely by small distances in the x- and y-directions and in rotation. Regardless of what means is used to stack the pipette racks, one or more additional pipette racks (not shown) may be stacked on top of pipette rack 400 before pipette rack 400 is stacked on pipette rack 300. Moreover, pipette rack 300 may be stacked on one or more other pipette racks before pipette rack 400 is stacked on top of it. Furthermore, instead of stacking pipette rack 400 on top of pipette rack 300, pipette rack 300 may be stacked under pipette rack 400. Finally, to simplify the following description, the nesting of the pipette tips in pipette rack 400 in the pipette tips in pipette tip 300 will be described with reference to the nesting of one exemplary pipette tip 30 in pipette rack 400 in one exemplary pipette tip 10 in pipette rack 300. The description is equally applicable to the nesting of the remaining pipette tips in pipette rack 400 in respective ones of the remaining pipette tips in pipette rack 300.

FIG. 6A shows pipette rack 400 early in the stacking process. Pipette rack 400 is shown roughly aligned relative to pipette rack 300 in the x-y plane. Pipette rack 400 has been lowered in the −z-direction so the proximal ends of pipette tips 10 and the proximal part of inner plate 321 have entered opening 446 bounded by skirt 440. The alignment of pipette rack 400 is such that the outer plate 323 of pipette rack 300 cannot enter opening 446, but is such that the distal end surface 444 of skirt 440 contacts stacking guide 390 located on the left-hand perimeter of the outer plate 323. Since the overall height of pipette rack 400 is greater than the overall length of pipette tips 30, outer plate 323 must enter opening 446 before the distal end 42 of pipette tip 30 in pipette rack 400 can enter the bore 13 of the neck portion 12 of pipette tip 10 in pipette rack 300.

FIG. 6B shows pipette rack 300 and pipette rack 400 after pipette rack 400 has been lowered further in the −z-direction. As pipette rack 400 is lowered relative to the position shown in FIG. 6A, those of the stacking guides 390 on the outer plate 323 of pipette rack 300 that engage with the skirt 440 of pipette rack 400 cause pipette rack 400 additionally to move in a direction that aligns opening 446 bounded by skirt 440 with outer plate 323. Such movement is in one or more of the x-direction, the y-direction and rotation. In the example shown, pipette rack 400 has moved in the −x-direction by a distance sufficient to allow a proximal portion of outer plate 323 to enter opening 446. Aligning pipette rack 400 in the x-y plane and in rotation such that outer plate 323 can enter opening 446 automatically aligns the distal end of pipette tip 30 in pipette rack 400 with the bore 13 of the neck portion 12 of pipette tip 10 in pipette rack 300 such that pipette tip 30 is nominally aligned coaxially with pipette tip 10. This alignment prevents the distal end of pipette tip 30 from contacting the proximal end of the collar 18 of pipette tip 10. As a result, when pipette rack 400 is lowered further in the −z-direction past the position shown in FIG. 6B, pipette tip 30 nests in pipette tip 10 with no significant physical contact between pipette tip 30 and pipette tip 10. Such physical contact could cause pipette tip 30 to move in the z-direction relative to pipette rack 400. Such movement of pipette tip 30 could eject pipette tip 30 from pipette rack 400 or could mis-orient pipette tip 30 in pipette rack 400 with an incorrect orientation, either of which could cause jamming when an additional pipette rack is stacked on pipette rack 400.

Skirt 440 has a inside surface 442 that, at the proximal end of skirt 440 adjacent base 430, provides a clearance fit with the side surface 338 of the base 330 of pipette rack 300. This clearance fit accurately defines the location of pipette rack 400 relative to pipette rack 300 in the x-y plane and in rotation when pipette rack 400 is stacked on pipette rack 300, as will be described below with reference to FIG. 6C. To guide the skirt 440 of pipette rack 400 into a final alignment with the outer plate 323 of pipette rack 300, the inside surface 442 of skirt 440 flares outward slightly with increasing distance from base 430. In the example shown in FIGS. 6A-6C, skirt 440 has a cross-sectional shape that tapers towards the end surface 444 of skirt 440 such that inside surface 442 flares outward. Alternatively, skirt 440 has a non-tapered cross-sectional shape and skirt 440 flares outwards as a whole in a manner similar to the skirt 140 of pipette rack 100 described above with reference to FIGS. 2A and 2B. The above description of skirt 440 additionally applies to skirt 340.

As noted above, the tip receptacles 350 in pipette rack 300 and the tip receptacles 450 in pipette rack 400 are contoured to provide a clearance fit with the pipette tip at locations axially offset from one another along the pipette tip. The closeness of the clearance fit depends on a number of factors, as described above with reference to FIGS. 3A and 3B. In pipette racks 300 and 400, the allowed range of the clearance fit between the tip receptacles and the pipette tips depends on the flare of the inside surface of the skirt. Stacking guides 390 and 490 increase the permissible range of the initial mis-alignment between pipette racks 300 and 400 (FIG. 6A) without reducing the allowed range of the clearance fit as would be required if the permissible range of the initial mis-alignment were increased by increasing the flare of the inside surface of the skirt. Stacking guides 390 on pipette rack 300 allow the inside surface 442 of the skirt 440 of pipette rack 400 to be flared less than in an embodiment in which the flaring of inside surface 442 was the only alignment aid, or even not to be flared at all.

FIG. 6C shows pipette rack 300 and pipette rack 400 at the end of the stacking process. The distal end surface 460 of the base 430 of pipette rack 400 and the end surfaces 437 of the buttresses 436 of pipette rack 400 rest on the outer first surface 327 of pipette rack 300. Contact between end surfaces 437 and 460 of pipette rack 400 and outer first surface 327 defines the location of pipette rack 400 relative to pipette rack 300 in the z-direction. Stacking guides 390 project above outer first surface 327, but each is located within one of the recessed portions 462 defined in base 430. Although the inside surface 442 of the skirt 440 of pipette rack 400 has a clearance fit with the side surface 338 of the base 330 of pipette rack 300, inside surface 442 typically makes contact with side surface 338 at about four spatially-separated locations. Contact between the inside surface 442 of skirt 440 and the side surface 338 of base 330 defines the location of pipette rack 400 relative to pipette rack 300 in the x-y plane and in rotation.

Pipette tip 30 in pipette rack 400 is nested in pipette tip 10 in pipette rack 300 without physical contact between them. Moreover, since there was no contact between pipette tip 30 and pipette tip 10 during the stacking process, the stacking process has not dislodged pipette tip 30 from its tip receptacle 450 in pipette rack 400. Nesting part of pipette rack 300 in part of pipette rack 400 and nesting part of pipette tip 30 in part of pipette tip 10 allows pipette racks 300 and 400 to be stacked with a stacking pitch that is less than the overall length of the pipette tips. In an example, pipette racks of pipette tips with an overall length of 26 mm were stacked with a stacking pitch of about 17 mm.

Base 430 has a height (z-direction dimension) from distal end surface 460 to outer plate 423 such that the height H3 of the second surface 424 of inner plate 421 above distal end surface 460 is greater than the sum of the height H5 of inner first surface 325 above outer first surface 327 and the maximum length L2 of the collars 18 of pipette tips 10. This dimensional relationship prevents contact, which is undesirable, between second surface 424 and the proximal ends of pipette tips 10 in pipette rack 300. In the example shown in FIG. 6C, the height of base 430 is such that the clearance between inner first surface 325 and second surface 424 is no more than that which accommodates the maximum length L2 of collars 18. In examples in which the pipette tips cannot be nested as closely as those exemplified in FIG. 6C, base 430 is configured such that the height H3 of second surface 424 above distal end surface 460 is greater than that of the example shown. In examples in which height H3 is increased, the height H4 of distal end surface 460 above distal end surface 444 is reduced so that the relationship between the overall height of pipette rack 400 and the length of pipette tips 30 remains unchanged. Heights H3, H4 and H5 are shown for pipette rack 300 in FIG. 5B.

Figure 7A:

FIGS. 7A-7E are schematic drawings showing an example of an automatic pipetting system 500 in which a robotic arm is used to automatically place a pipette rack loaded with pipette tips for engaging with the pipetting head of a pipetting station. FIG. 7A shows a robotic arm 510, a pipetting station 520 and rack stackers 530, 531 and 532 that constitute automatic pipetting system 500 located on a table 540. Robotic arm 510 is fitted at its distal end with a gripper 512 configured to engage with pipette racks. Gripper 512 has two opposed arms that engage with a pipette rack by clamping the base of the pipette rack between them. One of the arms constituting gripper 512 is shown at 514.

One or more of rack stackers 530, 531, 532 is used to dispense pipette racks from a nested stack of pipette racks in which the pipette racks and the pipette tips are nested as described above. Rack stacker 530 is shown holding a nested stack 600 of pipette racks, each similar to pipette rack 300 described above with reference to FIGS. 5A and 5B. The bottom pipette rack of nested stack 600 will be referred to as pipette rack 300. Nested stack 600 may alternatively be composed of pipette racks similar to pipette rack 100 described above with reference to FIGS. 2A and 2B. Another of rack stackers 530, 531, 532 is used to re-stack used pipette racks, which are pipette racks in which the pipette tips have been used.

Each of rack stackers 530, 531 and 532 has a respective presentation stage 534, 535 and 536. Rack stacker 530 that dispenses pipette racks of unused pipette tips deposits a single pipette rack taken from the bottom of nested stack 600 on presentation stage 534 for pick up by robotic arm 510. In rack stacker 531 that re-stacks used pipette racks containing used pipette tips, the robotic arm deposits a single used pipette rack on presentation stage 535. Rack stacker 531 then adds the newly-deposited used pipette rack to the bottom of the stack of used pipette racks stored therein.

Each of rack stackers 530, 531 and 532 additionally has a gripper (not shown) that clamps the sides of the base of the bottom pipette rack of the nested stack of pipette racks stored in the rack stacker to hold the nested stack in position within the rack stacker.

The example of automatic pipetting system 500 shown in FIGS. 7A-7E has three rack stackers 530, 531 and 532 of which only two are used in performing the protocol described below. Other examples have a different number of rack stackers, depending on the requirements of the particular protocol performed by automatic pipetting system 500.

Automatic pipetting system 500 additionally has a controller 560 that controls the operation of robotic arm 510, pipetting station 520, rack stackers 530, 531 and 532 and other elements of automatic pipetting system 500 to perform desired protocols. Controller 560 is embodied in any proprietary or commercially-available programmable device, such as, but not limited to, a computer with appropriate software. Controller 560 is programmed to provide commands to each element of system 500 to cause such element to perform the operations necessary for system 500 to perform one or more protocols. Such operations include robotic arm 510 moving pipette rack 300 from the presentation stage 534 of rack stacker 530 to pipetting station 520, and moving the used pipette rack 300 from the pipetting station to the presentation stage 535 of rack stacker 531 for re-stacking. In the following description of the operation of automatic pipetting station 500, the various elements of the automatic pipetting station operate in response to commands received from controller 560. Such commands are not described to simplify the description.

Pipetting station 520 has a pipetting head 550 configured to engage with the pipette tips in the pipette racks taken from the nested stack 600 of pipette racks stored in rack stacker 530. Pipetting station 520 is composed of a pipetting head 550, shelves 552, a press shelf 554 and a press table 556. Shelves 552 are used to support one of more of multi-well plates, rinsing stations, and/or pipette racks. In the example of pipetting station 520 shown in FIG. 7A, shelves 552 and press shelf 554 are movable left and right relative to pipetting head 550, pipetting head 550 is movable up and down relative to press shelf 554, and press table 556 is movable up and down relative to press shelf 554. Press shelf 554 defines a central aperture 555 through which press table 556 can move when press shelf 554 is aligned with the press table and the press table is moved upwards.

Figure 7B:

Although not shown in FIG. 7A, station base 180 described above with reference to FIG. 4 is mounted on press shelf 554 to receive the pipette racks transferred by robotic arm 510 from rack stacker 530. FIG. 7B shows station base 180 mounted on press shelf 554.

Operation of automatic pipetting system 500 will now be described with reference to FIGS. 7A-7E, and additionally to FIGS. 5A, 5B and 6A-6C. FIG. 7A shows automatic pipetting system 500 after it has performed the following operations. Presentation stage 534 of rack stacker 530 has moved up into contact with pipette rack 300 at the bottom of nested stack 600 of pipette racks stored within the rack stacker. The gripper of rack stacker 530 has released its grip on pipette rack 300, and presentation stage 534 has moved downwards until the next-to-bottom pipette rack in nested stack 600 is aligned with the gripper of rack stacker 530. The gripper of rack stacker 530 has clamped the base of the next-to-bottom pipette rack to hold the remainder of nested stack 600 in place in rack stacker 530. Presentation stage 534 on which pipette rack 300 is located has moved further downwards to separate pipette rack 300 from the remainder of nested stack 600. Finally, robotic arm 510 has moved gripper 512 towards the presentation stage 534 of rack stacker 530 and has operated gripper 512 to clamp the sides of the base 330 (FIG. 5A) of pipette rack 300 between its arms, one of which is shown at 514. Although not shown in FIG. 7A, robotic arm 510 next lifts pipette tip rack 300 from presentation stage 534 and carries the pipette rack towards pipetting station 520.

FIG. 7B shows automatic pipetting system 500 after robotic arm 510 has carried pipette rack 300 to pipetting station 520. Station base 180 has been mounted on press shelf 554, which is located at the right-hand end of its range of travel. Robotic arm 510 has placed pipette rack 300 on station base 180 located on tip press shelf 554. Although not shown in FIG. 7B, gripper 512 then releases pipette rack 300 and robotic arm 512 moves gripper 512 clear of pipette rack 300. Press shelf 554 then moves to the left to align station base 180 and pipette rack 300 with press table 556.

Figure 7C:

FIG. 7C shows automatic pipetting system 500 after press shelf 554 has moved to the left and pipetting head 550 has moved downwards. Referring additionally to FIGS. 7A and 7B, press shelf 554 has moved to the left to align station base 180 and pipette rack 300 with press table 556. Pipetting head 550 has moved downwards to bring the barrels (not shown) projecting downwards from the pipetting head into contact with the proximal ends of the pipette tips 10 (FIG. 7B) in pipette rack 300. Press table 556 then moves upwards through aperture 555 in press shelf 554 to contact the underside of station base 180. Further upward movement of press table 556 moves station base 180 and pipette rack 300 upwards to press the pipette tips 10 in pipette rack 300 onto the respective barrels of pipetting head 550. The force applied via the pipette tips to the inner plate 321 of pipette rack 300 is transferred to press table 556 via the base 330 (and, optionally, the buttresses 336) of pipette rack 300 and station base 180.

Although not shown in FIG. 7C, after the pipette tips 10 have engaged with the respective barrels of pipetting head 550, press table 556 is moved downwards, and pipetting head 550 is moved upwards. Initial downward movement of press table 556 puts station base 180 back in contact with press shelf 554. Further downward movement of press table 556 withdraws the press table from the aperture 555 of press shelf 554, which allows press shelf 554 to move laterally once more. Pipetting head 550 is then moved upwards, which withdraws pipette tips 10 from pipette rack 300.

FIG. 7D shows automatic pipetting system 500 after pipetting head 550 has moved upwards clear of the lateral movement path of the lowest one of shelves 552. Pipette tips 10 are engaged with pipetting head 550 and are ready for use in performing a procedure. Press shelf 554 on which station base 180 and pipette rack 300, now empty of pipette tips, are located, has moved to the right-hand end of its range of travel.

Figure 7E:

FIG. 7E shows a container 590 containing liquid that will be taken up by the pipette tips mounted on pipetting head 550 (FIG. 7D), and another container 592 into which the pipette tips mounted on the pipetting head will dispense the liquid. One or both of containers 590, 592 is segmented into wells each corresponding to one of the pipette tips. Containers 590, 592 are placed on respective ones of shelves 552. The shelf 552 on which container 590 is located is moved laterally to align the wells of the container 590 with respective ones of the pipette tips mounted on pipetting head 550. Pipetting head 550 is then moved downwards to locate the distal ends of the pipette tips below the level of the liquid in the container 590. Pipetting head 550 then draws a defined aliquot of the liquid into each of the pipette tips. Pipetting head 550 is then moved upwards until the distal ends of the pipette tips are clear of container 590. The shelf 552 on which container 590 is located is then moved laterally out of alignment with pipetting head 550. Pipetting head 550 is then moved upwards or downwards (upwards in the example shown) to a level at which the distal ends of the pipette tips are clear of container 592 into which the liquid held in the pipette tips will be deposited. The shelf 552 on which container 592 is located is moved laterally to align the wells of container 592 with the pipette tips mounted on pipetting head 550. Pipetting head 550 is then moved downwards towards container 592, and the liquid contained within each of the pipette tips is discharged from the pipette tips into a respective well of container 592. Pipetting head 550 is then moved upwards until the distal ends of the pipette tips are clear of container 592, and the shelf 552 on which container 592 is located is moved laterally out of alignment with pipetting head 550.

Press shelf 554 then moves to the left once more to align station base 180 and pipette rack 300 with pipetting head 550. Pipetting head 550 moves downwards to return the pipette tips 10 mounted thereon to pipette rack 300. Pipetting head 550 ejects the pipette tips 10 from their respective barrels. Once the pipette tips are ejected from the pipetting head, pipetting head 550 moves upwards until the distal ends of the barrels of the pipetting head are clear of the pipette tips so that press shelf 554, station base 180 and pipette rack 300 can move laterally. Press shelf 554 then moves station base 180 and pipette rack 300 containing used pipette tips 10 laterally to the right-hand end of its range of travel.

Robotic arm 510 then aligns gripper 512 at its distal end with pipette rack 300. Gripper 512 clamps the sides of the base 330 of pipette rack 300, and the robotic arm carries pipette rack 300 to the presentation stage 535 of rack stacker 531. Rack stacker 531 contains a partial stack (not shown) of pipette racks containing used pipette tips. Re-stacking without causing jamming is a capability of pipette racks in accordance with the invention and is not a capability of conventional pipette racks. Once robotic arm 510 has aligned pipette rack 300 with presentation stage 535, gripper 512 releases pipette rack 300, leaving pipette rack 300 on presentation shelf 535 with the distal end surface 344 of skirt 340 in contact with the presentation shelf. Robotic arm 510 then withdraws gripper 512 from the vicinity of presentation stage 535, and rack stacker 531 then performs a restacking operation.

At the start of the restacking operation, the partial nested stack of used pipette racks is held in place in rack stacker 531 by a gripper (not shown) that constitutes part of the rack stacker. The gripper clamps the sides of the base of the bottom pipette rack in the nested stack. The presentation shelf 535 of rack stacker 531 then moves upwards, bringing pipette rack 300 towards the bottom pipette rack in the nested stack. As pipette rack 300 approaches the bottom pipette rack, the stacking guides 390 on pipette rack 300 align pipette rack 300 in the x-y plane and in rotation with the opening bounded by the skirt of the bottom pipette rack in a manner similar to that described above with reference to FIGS. 6A and 6B. Further upward movement of presentation shelf 535 causes the pipette tips in the bottom pipette rack to nest in the pipette tips 10 in pipette rack 300, and brings the distal end surface of the base of the bottom pipette rack into contact with the outer plate 323 of pipette rack 300, also as described above. The gripper of rack stacker 531 then releases the bottom pipette rack, and presentation shelf 535 moves further upwards. This moves the nested stack of pipette racks, now including pipette rack 300 as a new bottom pipette rack, upwards within rack stacker 531. Presentation rack 535 stops moving upwards when pipette rack 300 is aligned with the gripper of rack stacker 531. The gripper of rack stacker 531 then clamps the sides of the base 330 of pipette rack 300 to hold the nested stack of used pipette racks containing used pipette tips in place within rack stacker 531.

The process just described repeats until the protocol performed by automatic pipetting system 500 is completed. Performing the protocol depletes, but does not necessarily exhaust, the nested stack 600 of new pipette racks containing unused pipette tips in rack stacker 530, and adds to the nested stack of used pipette racks containing used pipette tips in rack stacker 531. Before another protocol is performed, the nested stack of used pipette racks is removed from rack stacker 531 for re-use or recycling. Since nested stack of used pipette racks removed from rack stacker 531 has a format similar to that of a nested stack of new pipette racks, the nested stack of used pipette racks can be removed easily and quickly and packaging used for a nested stack of new pipette racks can be used to package the nested stack of used pipette racks. Conventional used pipette racks have to be disposed of individually.

Moreover, with conventional pipette racks, any unused pipette racks remaining in rack stacker 530 would have to be removed and discarded before a new nested stack of pipette racks can be added. However, with pipette racks in accordance with embodiments of the invention, a partial or full nested stack of new pipette racks can be added to the partial nested stack of new pipette racks remaining in rack stacker 530 to provide a new nested stack containing the number of pipette racks needed to perform the next one or more protocols. The nested stack of new pipette racks is inserted into rack stacker 530 from the top and is lowered into place on top of the remaining pipette racks, i.e., the pipette racks that remain within rack stacker 530. The bottom pipette rack on the stack of additional pipette racks stacks on top of the top pipette rack of the remaining pipette racks, and the pipette tips in the bottom pipette rack nest in the pipette tips in the top pipette rack in the manner described above.

A method 700 in accordance with an embodiment of the invention will now be described with reference to FIG. 8A. In 710, an automatic pipetting system comprising a robotic arm, a pipetting station and a rack stacker is provided. In 720, a nested stack of pipette racks is provided. In the nested stack, pipette tips in a first one of the pipette racks are nested within pipette tips in a second one of the pipette racks on which the first one of the pipette racks is stacked. In 730, the nested stack of pipette racks is loaded into the rack stacker. In 740, a pipetting protocol is performed using the automatic pipetting system. Performing the protocol leaves some of the pipette racks remaining in the rack stacker. In 750, additional pipette racks are stacked on the remaining pipette racks in the rack stacker to form a new nested stack of pipette racks. In stacking the additional pipette racks, pipette tips in one of the additional pipette racks are nested in pipette tips in one of the remaining pipette racks. In 760, another protocol is performed.

In a variation, in 710, the rack stacker is a first rack stacker and a second rack stacker is additionally provided. Then, as illustrated in FIG. 8B, in performing the protocol shown in block 740 of FIG. 8A, in 741, pipette racks are transferred from the first rack stacker to the pipetting station using the robotic arm; in 743, the pipette racks are transferred from the pipetting station to the second rack stacker using the robotic arm; and, in 745, the pipette racks are re-stacked in the second rack stacker to form a nested stack of pipette racks. Re-stacking the pipette racks involves nesting pipette tips in one of the pipette racks transferred to the second rack stacker by one operation of the robotic arm in pipette tips in one of the pipette racks transferred to the second rack stacker by another operation of the robotic arm.

This disclosure describes the invention in detail using illustrative embodiments. However, the invention defined by the appended claims is not limited to the precise embodiments described.

We claim:

1. A nestable, stackable pipette rack for nestable pipette tips, the pipette rack comprising:
   a plate comprising a first surface and defining an array of tip receptacles extending through the plate in a first direction orthogonal to the first surface, the tip receptacles comprise a contoured inside wall to provide a tapered clearance fit matching a tapered part of a pipette tip located therein for automated operations;
   a peripheral base extending in the first direction from the plate to a distal end surface; and
   a peripheral skirt extending from the base in the first direction, the skirt outwardly offset from the base to expose at least part of the distal end surface of the base, the distal end surface contacting the plate of another, similar pipette rack when the pipette racks are stacked.

2. The pipette rack of claim 1, in which the skirt comprises an inside surface that flares outwardly with increasing distance from the plate.

3. The pipette rack of claim 1, in which the base is configured such that the distal end surface thereof contacts the plate of the other pipette rack when the pipette racks are stacked.

4. The pipette rack of claim 3, in which:
   the plate comprises an inner plate and an outer plate around at least part of the inner plate;
   the tip receptacles are defined in the inner plate;
   the inner plate has an inner first surface, the outer plate has an outer first surface, and
   the outer first surface is offset in the first direction from inner first surface; and
   the base extends in the first direction from the outer plate.

5. The pipette rack of claim 4, additionally comprising buttresses connecting the inner plate to the outer plate and the base.

6. The pipette rack of claim 5, in which the buttresses have respective end surfaces flush with the distal end surface of the base.

7. The pipette rack of claim 6, additionally comprising alignment guides at a perimeter of the outer first surface of the plate.

8. The pipette rack of claim 1, additionally comprising alignment guides at a perimeter of the first surface of the plate.

9. A combination, comprising:
   a pipette tip comprising a hollow neck portion and a hollow tapered portion extending distally from the neck portion, the neck portion comprising a bore dimensioned to accommodate at least part of the tapered portion of another, similar pipette tip; and
   a nestable, stackable pipette rack, comprising:
   a plate comprising a first surface and defining an array of tip receptacles extending through the plate in a first direction orthogonal to the first surface, the tip receptacles comprise a contoured inside wall to provide a tapered clearance fit matching a tapered part of the pipette tip for automated operations;
   a peripheral base extending in the first direction from the plate to a distal end surface; and
   a peripheral skirt extending from the base in the first direction, the skirt outwardly offset from the base to expose at least part of the distal end of the base, the distal end surface contacting the plate of another, similar pipette rack when the pipette racks are stacked; in which:
   when another, similar pipette rack is stacked on the pipette rack, the tapered portion of a pipette tip in the other pipette rack nests within the neck portion of the pipette tip without contacting the pipette tip.

10. The combination of claim 9, in which the skirt comprises an inside surface that flares outwardly with increasing distance from the plate.

11. The combination of claim 9, in which:
    the pipette tip has a length L1 from a collar surface to a distal end of the pipette tip;
    the plate additionally comprises a second surface parallel to the first surface; and
    length L1 is greater than a height H1 of the second surface of the plate above the first surface of the plate.

12. The combination of claim 11, in which length L1 is less than an overall height H of the first surface of the plate above a distal end of the skirt to prevent contact between the distal end of the pipette tip and a plane surface on which the pipette rack is placed.

13. The combination of claim 12, in which:
    the collar of the pipette tip has a length L2; and
    length L2 is less than a height H3 of the second surface of the plate above the distal end surface of the base.

14. The combination of claim 9, in which the base is configured such that the distal end surface thereof contacts the plate of the other pipette rack when the pipette racks are stacked.

15. The combination of claim 14, in which:
    the plate comprises an inner plate and an outer plate around at least part of the inner plate;
    the tip receptacles are defined in the inner plate;
    the inner plate has an inner first surface, the outer plate has an outer first surface, and the outer first surface is offset in the first direction from inner first surface; and
    the base extends in the first direction from the outer plate.

16. The combination of claim 15, in which the pipette rack additionally comprises buttresses connecting the inner plate to the outer plate and the base.

17. The combination of claim 16, in which the buttresses have respective end surfaces flush with the distal end surface of the base.

18. The combination of claim 17, in which the pipette rack additionally comprises alignment guides at a perimeter of the outer first surface of the plate.

19. The combination of claim 9, in which the pipette rack additionally comprises alignment guides at a perimeter of the first surface of the plate.

20. A method, comprising:
    providing an automatic pipetting system comprising a robotic arm, a pipetting station and a rack stacker;
    providing a nested stack of pipette racks in which pipette tips in a first one of the pipette racks are nested within pipette tips in a second one of the pipette racks on which the first one of the pipette racks is stacked; wherein the pipette rack comprises a plate comprising a first surface and defining an array of tip receptacles extending through the plate in a first direction orthogonal to the first surface, the tip receptacles comprise a contoured inside wall to provide a tapered clearance fit matching a tapered part of a pipette tip located therein for automated operations;
    loading the nested stack of pipette racks into the rack stacker;
    performing a protocol using the automatic pipetting system, the protocol moves a first pipette rack from the nested stack of pipette racks, the performing leaving remaining pipette racks in the rack stacker;
    stacking additional pipette racks on the remaining pipette racks in the rack stacker to form a new nested stack of pipette racks, the stacking comprising nesting pipette tips in one of the additional pipette racks in pipette tips in one of the remaining pipette racks; and performing a new protocol.

21. The method of claim 20, in which:

the rack stacker is a first rack stacker;

the automatic pipetting system additionally comprises a second rack stacker; and the performing comprises:

transferring the pipette racks from the first rack stacker to the pipetting station using the robotic arm, transferring the pipette racks from the pipetting station to the second rack stacker using the robotic arm; and re-stacking the pipette racks in the second rack stacker to form a nested stack of pipette racks, the re-stacking comprising nesting pipette tips in one of the pipette racks transferred to the second rack stacker by one operation of the robotic arm in pipette tips in one of the pipette racks transferred to the second rack stacker by another operation of the robotic arm.

* * * * *